United States Patent [19]

Lantos

[11] 4,096,247

[45] Jun. 20, 1978

[54] GOLD THIO GLUCOPYRANOSIDE COMPOUNDS AND METHOD OF USE

[75] Inventor: Ivan Lantos, Blackwood, N.J.

[73] Assignee: SmithKline Corporation, Philadelphia, Pa.

[21] Appl. No.: 769,146

[22] Filed: Feb. 16, 1977

[51] Int. Cl.$^2$ .................... A61K 31/70; C07H 11/04
[52] U.S. Cl. .................................. 424/180; 536/117; 536/118; 536/121; 536/122
[58] Field of Search ............... 536/117, 118, 121, 122; 424/180

[56] References Cited

U.S. PATENT DOCUMENTS 3,635,945  1/1972  Nemeth et al. ................. 536/121

Primary Examiner—Johnnie R. Brown
Attorney, Agent, or Firm—William H. Edgerton

[57] ABSTRACT

A new series of lower alkyl ethers of S-tri-lower-alkyl-phosphinegold 1-thio-$\beta$-D-glucopyranoside has been prepared and found to have anti-arthritic activity and, in particular, are of use in the treatment of rheumatoid arthritis.

7 Claims, No Drawings

GOLD THIO GLUCOPYRANOSIDE COMPOUNDS AND METHOD OF USE

This invention relates to a new series of organic gold compounds whose structures are characterized in that they are tetra-lower alkyl ethers of S-tri-lower-alkylphosphinegold (I) 1-thio-$\beta$-D-glucopyranosides. These new compounds have anti-arthritic activity and, in particular, are of use in the treatment of rheumatoid arthritis.

It is known in the prior art that certain gold containing glucopyranosides have oral anti-arthritic activity (U.S. Pat. No. 3,635,945). The compounds of this prior art patent are limited to the 1-thio-$\beta$-D-glucopyranoside phosphinegold complexes in the tetrahydroxy or tetra-O-acetyl form. There is no disclosure in this patent of any O-ethers of glucopyranoside phosphinegold complexes and no suggestion that ethers would have any anti-arthritic activity.

The compounds of this invention are the tetra-O-lower alkyl ethers of S-tri-lower-alkylphosphinegold (I) 1-thio$\beta$-D-glucopyranoside. They are illustrated by the following structural formula:

$$\text{Structure I: CH}_2\text{OR, O, SAuP(R}_1)_3, \text{OR, RO, OR}$$

in which:

R is lower alkyl of 1–4 carbon atoms preferably methyl; and $R_1$ is lower alkyl of 1–4 carbon atoms preferably ethyl.

The compounds of this invention are prepared by reacting a 1-thio-2,3,4,6-tetra-O-lower alkyl-$\beta$-D-glucopyranose with a halo (tri-lower-alkylphosphine)-gold(I) in the presence of a base such as an alkali metal carbonate or bicarbonate in an inert organic solvent mixture in which the reactants are soluble such as an aqueous lower alkanol as ethanol or methanol. The reaction is often run at cool temperatures such as from −20° up to ambient or room temperature for up to 2–5 hours. The product is isolated from the reaction mixture by methods common in the art.

The starting material 1-thio-2,3,4,6-tetra-O-lower alkylglucopyranoses are prepared by reacting the known 1-bromo congener with thiourea most conveniently in an inert solvent in which the reactants are soluble such as acetone. The intermediate thiopseudourea is then split with sodium bisulfite to give the desired 1-thio starting material.

the halo (tri-lower-alkylphosphine)gold(I) compounds which are the other starting materials are prepared as described in U.S. Pat. No. 3,635,945.

The compounds of this invention are useful in treatment of arthritis. This activity is demonstrated by the following test procedure.

Inhibition of adjuvant induced polyarthritis in rats, as measured by reduction of rat paw edema, is produced by compounds of this invention such as S-triethylphosphinegold 2,3,4,6-tetra-O-methyl-1-thio-$\beta$-D-glucopyranose at daily oral doses of about 20 mg/kg (calculated on gold content). In this test procedure, adjuvant arthritis in rats is produced by a single intradermal injection of 0.75 mg of *Mycobacterium butyricum* suspended in white paraffin oil into the left hindpaw footpad. The injected paw becomes inflamed (increased volume) and reaches maximal size within three to five days (primary lesion). The animals exhibit a decrease in body weight gain during the initial period. The adjuvant arthritis (secondary lesion) occurs after approximately ten days and is characterized by inflammation of the non-injected right hind leg, decrease in body weight, and further increase in the volume of the injected left hind leg. Test compounds are administered daily, beginning on the day of the adjuvant injection, for 17 days thereafter, exclusive of days 4, 5, 11 and 12. Anti-arthritic activity is shown by the ability to inhibit the development of either primary or secondary lesions of adjuvant arthritis. Auranofin which is a clinically effective anti-arthritic is active in this test procedure at doses of from 10–20 mg/kg orally.

The compounds of this invention are administered in conventional dosage forms prepared by combining a compound of Formula I in a nontoxic amount sufficient to produce anti-arthritic activity with standard pharmaceutical carriers according to conventional procedures. These procedures may involve mixing, granulating and compressing or dissolving the ingredients as appropriate to the desired preparation. The resulting pharmaceutical compositions are also objects of this invention. Oral dosage forms are preferred.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or duluent may include time delay material well known to the art, such as glyceryl monostearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 g. If a liquid carrier is used, the preparation will be in the form of a syrup, emulsion, soft gelatin capsule, sterile injectable liquid such as an ampule or nonaqueous liquid suspension.

Preferably, each dosage unit will contain the active ingredient in an amount of from about 1 mg to about 10 mg.

The method of producing anti-arthritic activity by administering internally to an animal a compound of Formula I is also an object of this invention. The compound of Formula I is administered in an amount sufficient to produce anti-arthritic activity but have no limiting side effects. The route of administration is preferably oral. The daily dosage regimen will be preferably from about 1 mg to about 12 mg most often in one or two oral doses daily. When the method is carried out as described above, anti-arthritic activity is produced in a subject afflicted with arthritic symptoms, for example in humans or in domestic animals such as dogs.

One skilled in the art will recognize that in determining the amounts of the active ingredient in the claimed compositions and used in the claimed methods, the activity of the chemical ingredient as well as the size and condition of the host animal must be considered.

The amounts given above are calculated for the average human subject.

The term "lower alkyl" where used herein denote groups having preferably 1–4 carbon atoms preferably methyl.

The following examples are not limiting but are illustrative of the invention. Any melting points are in degrees Centigrade.

EXAMPLE 1

1-Bromo-2,3,4,6-tetra-O-methyl-β-D-glucopyranose (10 g), prepared according to the method of Levene et al. [J. Biol. Chem., 98, 17 (1932)] was dissolved in 50 ml acetone and 2.90 g of thiourea was added. The displacement reaction was allowed to proceed under reflux until a tlc sample no longer detected the presence of the bromoglucose starting material (2–2½ hours). The solution was cooled, the solvent was removed under reduced pressure, and the resultant oil was taken up in 50 ml of water and heated to 85°–90° on the steam bath. Sodium bisulfite (10 g) was added in one portion, the temperature of the mixture was maintained for five minutes with constant swirling and heating was discontinued. The solution was allowed to cool to room temperature, it was saturated with sodium sulfate and extracted with chloroform. The oily 1-thio-2,3,4,6-tetra-O-methyl-β-D-glucopyranose obtained by evaporation of the dried organic extracts, 5.0 g, was used directly in the next step.

1-Thio-2,3,4,6-tetra-O-methyl-β-D-glucopyranose (1.66 g) was dissolved in 18 ml of water and a solution of 1.0 g of potassium carbonate in 12 ml of water was added. The mixture was cooled to −15° and 2.3 g of chloro (triethyl-phosphine)gold(I) was added in 18 ml of ethanol. Cooling, and stirring was maintained for 1½ hours. The mixture was allowed to come to ambient temperature. The solution was concentrated at reduced pressure then was partitioned between water and methylene chloride. The organic extract was dried over magnesium sulfate, fultered, and concentrated to a viscous oil which was chromatographed by dry-column chromatography over silica gel using ethyl acetate as eluent. Yield: 1.7 g of S-triethylphosphinegold(I) 2,3,4,6-tetra-O-methyl-1-thio-β-D-glucopyranoside in the form of an oily liquid.

$C_{16}H_{34}O_5PSAu$

| | |
|---|---|
| Calculated: | 33.92% C; 6.05% H; 5.47% P |
| Found: | 33.82% C; 6.18% H; 5.45% P |
| IR(Nujol, cm$^{-1}$): | 1099 (several str. bands C-O), 775–763 (m, PEt$_3$) |
| NMR(CDCl$_3$, d): | 6.05 (d, J = 6, 1H), 4.7 (d, J = 9, 1H), 4.45 (dt, J = 9,2; 2H), 3.70–3.35 (4 singlets, 4CH$_3$O), 2.1–0.9 (multiplet, PEt$_3$) |

EXAMPLE 2

Substituting equivalent amounts of chloro (triisopropylphosphine)gold(I), chloro (tributylphosphine)-gold(I) or chloro (trimethylphosphine)gold(I) in the final step of Example 1 gives S-triisopropylphosphinegold(I) 2,3,4,6-tetra-O-methyl-1-thio-β-D-glucopyranoside, S-tributylphosphinegold(I) 2,3,4,6-tetra-O-methyl-1-thio-β-D-glucopyranoside or S-trimethylphosphinegold(I) 2,3,4,6-tetra-O-methyl-1-thio-β-D-glucopyranoside.

EXAMPLE 3

Substituting an equivalent amount of 1-bromo-2,3,4,6-tetra-O-ethyl-β-D-glucopyranose in Example 1 gives S-triethylphosphinegold(I) 2,3,4,6-tetra-O-ethyl-1-thio-β-D-glucopyranoside. Substituting an equivalent amount of 1-bromo-2,3,4,6-tetra-O-isopropyl-β-D-glucopyranose gives S-triethyl-phosphinegold(I) 2,3,4,6-tetra-O-isopropyl-1-thio-β-D-glucopyranoside.

EXAMPLE 4

| Ingredients | Amounts |
|---|---|
| S-triethylphosphinegold(I) 2,3,4,6-tetra-O-methyl-1-thio-β-D-glucopyranoside | 5 mg |
| magnesium stearate | 5 mg |
| lactose | 140 mg |

The above ingredients are mixed, screened and filled into a hard gelatin capsule. The capsule is administered orally twice daily to a human subject having arthritis.

EXAMPLE 5

| Ingredients | Amounts |
|---|---|
| S-triethylphosphinegold(I) 2,3,4,6-tetra-O-methyl-1-thio-β-D-glucopyranoside | 6 mg |
| Peanut Oil | 94 mg |

The ingredients are mixed and filled into a soft gelatin capsule which is administered orally to a subject in need of treatment once a day. If no improvement is noted, the dose is increased until either improvement is noted or toxic effects preclude further increase in dosage.

What is claimed is:

1. A chemical compound of the formula:

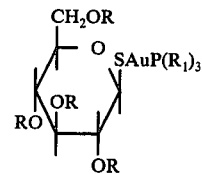

in which:

R and R$_1$ are each respectively lower alkyl of 1–4 carbons.

2. A compound of claim 1 in which R is methyl.

3. A compound of claim 1 in which R is methyl and R$_1$ is ethyl.

4. A pharmaceutical composition having anti-arthritic activity, in dosage unit form, comprising a pharmaceutical carrier and an effective amount of a compound of claim 1.

5. A method of producing anti-arthritic activity which comprises administering internally to a subject in need of treatment an effective amount of a compound of claim 1.

6. The method of claim 5 in which the compound is S-triethylphosphinegold(I) 2,3,4,6-tetra-O-methyl-1-thio-β-D-glucopyranoside which is administered orally.

7. The method of claim 6 in which the daily dosage is chosen from the range of from 1–12 mg of active ingredient.

* * * * *